United States Patent
Shimazu et al.

(10) Patent No.: US 9,365,492 B2
(45) Date of Patent: Jun. 14, 2016

(54) 2-(ETHYLAMINO)ETHANOL PRODUCTION METHOD

(71) Applicant: KOEI CHEMICAL COMPANY, LIMITED, Osaka (JP)

(72) Inventors: Hidetaka Shimazu, Chiba (JP); Tsuyoshi Tagata, Chiba (JP)

(73) Assignee: KOEI CHEMICAL COMPANY, LIMITED, Osaka (JP)

(*) Notice: Subject to any disclaimer, the term of this patent is extended or adjusted under 35 U.S.C. 154(b) by 0 days.

(21) Appl. No.: 14/436,026

(22) PCT Filed: Oct. 2, 2013

(86) PCT No.: PCT/JP2013/005875
§ 371 (c)(1),
(2) Date: Apr. 15, 2015

(87) PCT Pub. No.: WO2014/061219
PCT Pub. Date: Apr. 24, 2014

(65) Prior Publication Data
US 2015/0266807 A1    Sep. 24, 2015

(30) Foreign Application Priority Data
Oct. 17, 2012  (JP) ................................. 2012-229465

(51) Int. Cl.
*C07C 213/08* (2006.01)
*B01J 21/10* (2006.01)
*B01J 23/04* (2006.01)

(52) U.S. Cl.
CPC ............... *C07C 213/08* (2013.01); *B01J 21/10* (2013.01); *B01J 23/04* (2013.01)

(58) Field of Classification Search
None
See application file for complete search history.

(56) References Cited

U.S. PATENT DOCUMENTS

| 2002/0115890 A1* | 8/2002 | Melder ................ C07C 213/00 564/470 |
| 2010/0087685 A1 | 4/2010 | King et al. |

FOREIGN PATENT DOCUMENTS

| JP | 07-033718 | 2/1995 |
| JP | 09-268163 | 10/1997 |
| JP | 2004-275933 | 10/2004 |
| WO | 2009/145280 | 12/2009 |

OTHER PUBLICATIONS

International Search Report for PCT/JP2013/005875, dated Jan. 7, 2014.
Extended European Search Report issued Apr. 21, 2016 in corresponding European Application No. 13847730.2.

\* cited by examiner

*Primary Examiner* — Sudhakar Katakam
*Assistant Examiner* — Jennifer C Sawyer
(74) *Attorney, Agent, or Firm* — Wenderoth, Lind & Ponack, L.L.P.

(57) ABSTRACT

The present invention relates to a production method for 2-(ethylamino)ethanol, including subjecting N-ethyldiethanolamine to a disproportionation reaction in the presence of at least one kind of catalyst selected from the group consisting of a manganese oxide catalyst and an alkali metal hydroxide-supporting zirconium oxide catalyst. According to the present invention, 2-(ethylamino)ethanol can be obtained by subjecting N-ethyldiethanolamine to the disproportionation reaction. 2-(Ethylamino)ethanol is a useful compound to be used in various applications such as a drug, an agricultural chemical, and a functional chemical.

18 Claims, No Drawings

2-(ETHYLAMINO)ETHANOL PRODUCTION METHOD

TECHNICAL FIELD

The present invention relates to a production method for 2-(ethylamino)ethanol, including subjecting N-ethyldiethanolamine to a disproportionation reaction in the presence of at least one kind of catalyst selected from the group consisting of a manganese oxide catalyst and an alkali metal hydroxide-supporting zirconium oxide catalyst. 2-(Ethylamino)ethanol is a useful compound to be used in various applications such as a drug, an agricultural chemical, and a functional chemical.

BACKGROUND ART

As a production method for 2-(ethylamino)ethanol, there is known a method involving subjecting ethylene oxide and ethylamine to a reaction in the presence of a crystalline metallosilicate catalyst such as a zeolite (see, for example, Patent Literature 1).

CITATION LIST

Patent Literature

[PTL 1] JP 2004-275933 A

SUMMARY OF INVENTION

Technical Problem

In the above-mentioned production method for 2-(ethylamino)ethanol, 2-(ethylamino)ethanol, which is generated through a reaction between one molecule of ethylene oxide and one molecule of ethylamine, and N-ethyldiethanolamine, which is generated through a reaction between two molecules of ethylene oxide and one molecule of ethylamine, are both generated. A ratio between 2-(ethylamino)ethanol and N-ethyldiethanolamine to be generated through those reactions is as follows according to Examples of Patent Literature 1: 2-(ethylamino)ethanol:N-ethyldiethanolamine=about 50:50 to 80:20 (mol:mol).

As described above, in the method involving subjecting ethylene oxide and an excess of ethylamine to a reaction in the presence of a crystalline metallosilicate catalyst, 2-(ethylamino)ethanol and N-ethyldiethanolamine are simultaneously generated. Accordingly, it is difficult to selectively obtain only 2-(ethylamino)ethanol. In addition, N-ethyldiethanolamine has an application as, for example, a raw material for N-ethylmorpholine, but is not in very high demand. Therefore, it has been desired to develop a method of obtaining 2-(ethylamino)ethanol from the by-product N-ethyldiethanolamine.

An object of the present invention is to provide a method capable of solving the problem of the related-art method described above, that is, a method of producing 2-(ethylamino)ethanol from N-ethyldiethanolamine.

Solution to Problem

The inventors of the present invention have made intensive investigations in order to achieve the object. As a result, the inventors have found that 2-(ethylamino)ethanol is obtained by subjecting N-ethyldiethanolamine to a disproportionation reaction in the presence of at least one kind of catalyst selected from the group consisting of a manganese oxide catalyst and an alkali metal hydroxide-supporting zirconium oxide catalyst. Thus, the inventors have completed the present invention.

That is, the present invention relates to a production method for 2-(ethylamino)ethanol, including subjecting N-ethyldiethanolamine to a disproportionation reaction in the presence of at least one kind of catalyst selected from the group consisting of a manganese oxide catalyst and an alkali metal hydroxide-supporting zirconium oxide catalyst.

Advantageous Effects of Invention

According to one embodiment of the present invention, 2-(ethylamino) ethanol can be obtained from N-ethyldiethanolamine. Therefore, the present invention is industrially useful.

DESCRIPTION OF EMBODIMENTS

The present invention is described in detail below. In the present invention, 2-(ethylamino)ethanol is obtained by subjecting N-ethyldiethanolamine to a disproportionation reaction in the presence of at least one kind of catalyst selected from the group consisting of a manganese oxide catalyst and an alkali metal hydroxide-supporting zirconium oxide catalyst. The disproportionation reaction may be performed as any one of a liquid-phase disproportionation reaction and a gas-phase disproportionation reaction. It is preferred to adopt the liquid-phase disproportionation reaction on a small scale, and to adopt the gas-phase disproportionation reaction on a large scale.

In the present invention, N-ethyldiethanolamine is used as a raw material. The N-ethyldiethanolamine to be used is generally produced through the reaction between ethylene oxide and ethylamine described above, but N-ethyldiethanolamine other than that obtained by such method may be used. N-Ethyldiethanolamine may be dissolved in water or an appropriate solvent before being used for the disproportionation reaction. N-Ethyldiethanolamine is a liquid having a high viscosity at room temperature, and hence is preferably supplied to a reactor as a solution by being dissolved in a solvent so that the supply can be precisely performed at a constant rate. Examples of the solvent to be used include water, methanol, ethanol, isopropanol, butanol, tetrahydrofuran, benzene, toluene, and xylene. Of those, water is preferably used. The concentration of N-ethyldiethanolamine in the solution is not particularly limited.

In the present invention, a manganese oxide catalyst or an alkali metal hydroxide-supporting zirconium oxide catalyst is used as a catalyst. The catalyst may contain an element such as tin, zinc, copper, nickel, cobalt, iron, manganese, chromium, vanadium, titanium, zirconium, molybdenum, silver, lead, tungsten, or palladium.

Examples of the manganese oxide catalyst include manganese(II) oxide [MnO], manganese(III) oxide [$Mn_2O_3$], manganese(IV) oxide [$MnO_2$], and manganese(II, III) oxide [$Mn_3O_4$]. Of those, manganese (IV) oxide is preferred. As the manganese oxide catalyst, a commercially available one may be used, or one prepared in advance may be used. As a method of preparing the manganese oxide catalyst, there is given, for example, a preparation method involving oxidizing manganese nitrate with air.

Examples of the alkali metal hydroxide-supporting zirconium oxide catalyst include a lithium hydroxide-supporting zirconium oxide catalyst, a potassium hydroxide-supporting zirconium oxide catalyst, a sodium hydroxide-supporting zirconium oxide catalyst, a cesium hydroxide-supporting zirconium oxide catalyst, and a rubidium hydroxide-supporting zirconium oxide catalyst. Of those, a potassium hydroxide-supporting zirconium oxide catalyst and a sodium hydroxide-supporting zirconium oxide catalyst are preferred. As a method of preparing the alkali metal hydroxide-supporting zirconium oxide catalyst, there is given a method involving adding zirconium oxide to an aqueous solution of an alkali metal hydroxide to impregnate the zirconium oxide with the alkali metal hydroxide, followed by drying and firing.

The manganese oxide catalyst or the alkali metal hydroxide-supporting zirconium oxide catalyst to be used may be supported on a support. The support is not limited as long as the support is one to be used in general catalyst preparation. Examples of the support include alumina, silica, zirconium oxide, magnesium oxide, cerium oxide, titanium oxide, and various zeolites.

As a method of preparing the catalyst other than the above-mentioned methods, any preparation method such as a kneading method, an impregnation method, or a coprecipitation method may be adopted. As a method of shaping the catalyst, any method such as extrusion into an arbitrary shape, or tableting may be adopted. The catalyst shaped by the method may be used after being fired under an atmosphere of an arbitrary gas such as air or nitrogen at a temperature of from 150 to 500° C.

The disproportionation reaction is performed at a temperature of generally from 100 to 500° C., preferably from 300 to 450° C., more preferably from 325 to 400° C. A reaction pressure may be any one of normal pressure and increased pressure. The mode of the disproportionation reaction is not particularly limited, and any one of fixed bed, fluidized bed, and moving bed modes may be adopted.

In the present invention, when a reaction aid is allowed to be present in the reaction system, the yield of 2-(ethylamino) ethanol is improved. Examples of the reaction aid include nitrogen-containing compounds such as ethylamine, ammonia, and a mixture thereof. The reaction aid is used in an amount of generally 0.2 mol or more, preferably from 0.5 to 5 mol, more preferably from 1 to 3 mol with respect to 1 mol of N-ethyldiethanolamine.

When the reaction aid is used, N-ethyldiethanolamine and the reaction aid are generally mixed and then introduced into a reactor as a mixture. The space velocity of the mixture in the reactor is generally from 0.01 to 2 (g/cc-catalyst·h), preferably from 0.1 to 1 (g/cc-catalyst·h) in terms of liquid hourly space velocity (LHSV). A value for the LHSV of N-ethyldiethanolamine when the reaction aid is not used is similar to the foregoing.

The disproportionation reaction is performed in the presence or absence of a diluent. Any diluent may be used without any particular limitation as long as the diluent is inert to the reaction. For example, the following substances may specifically be used: inert gases such as nitrogen and argon; aliphatic hydrocarbons such as hexane, heptane, octane, nonane, decane, and undecane; halogenated aliphatic hydrocarbons such as dichloromethane and 1,2-dichloroethane; water; and hydrogen. One kind of those substances may be used alone, or two or more kinds thereof may be used as a mixture.

In the disproportionation reaction, when a small amount of oxygen or air is allowed to coexist with the diluent, the yield of 2-(ethylamino)ethanol is improved. A molar ratio between the diluent and oxygen is generally from 1,000:1 to 10:1.

The 2-(ethylamino)ethanol generated through the disproportionation reaction may be collected by general means such as cooling of a reacted gas to be obtained through the disproportionation reaction, or absorption of the reacted gas into a solvent. Examples of the solvent include water, methanol, ethanol, isopropanol, butanol, tetrahydrofuran, benzene, toluene, and xylene. Of those, water is preferably used, and ice-cold water cooled with ice or the like is particularly preferred. The collected 2-(ethylamino)ethanol may be isolated or purified by general purification means such as distillation.

EXAMPLES

Next, the present invention is specifically described byway of Examples. However, the present invention is by no means limited to Examples described below. It should be noted that analysis by gas chromatography in Examples was performed under the following conditions.

Analysis Conditions for Gas Chromatography
Gas chromatograph: GC-2010 manufactured by Shimadzu Corporation,
Detector: FID
Column: HP-1 manufactured by J&W, 50 m, inner diameter: 0.32 mm,
film thickness: 1.05 μm
Temperature: 50° C.→(10° C./min)→250° C.

In addition, a conversion rate and a yield were calculated on the basis of the following definitions.

Conversion rate (%)=Reacted N-ethyldiethanolamine (mol)/N-ethyldiethanolamine fed for reaction (mol)×100

Yield (%)=Generated 2-(ethylamino)ethanol (mol)/N-ethyldiethanolamine fed for reaction (mol)×100

Example 1

Preparation of 0.5 wt % Potassium Hydroxide-Supporting Zirconium Oxide Catalyst

To 25 g of a 2% potassium hydroxide aqueous solution, 100 g of a zirconium oxide catalyst RSC-H pellet (cylindrical shape measuring 3.2 mm in diameter by 2.9 mm in length) manufactured by Daiichi Kigenso Kagaku Kogyo Co., Ltd. was added, and the contents were thoroughly mixed and then left to stand still for 30 minutes to impregnate the zirconium oxide catalyst with potassium hydroxide. The resultant mixture was dried at 120° C. for 2 hours, and then fired in a stream of air at 500° C. for 5 hours. Thus, a 0.5 wt % potassium hydroxide-supporting zirconium oxide catalyst was obtained.

Production of 2-(Ethylamino)ethanol

A cylindrical reactor having an inner diameter of 19 mm was loaded with 7.5 ml of the 0.5 wt % potassium hydroxide-supporting zirconium oxide catalyst, and was loaded with a 12-cm length each of Carborundum in the form of particles each having a diameter of from 2 to 3 mm on and below the catalyst. The reactor was heated to a temperature of 350° C. and purged with nitrogen, and then a mixed gas of nitrogen at 30 ml/min and air at 10 ml/min was flowed as a diluent. A 30 wt % aqueous solution of a mixture of N-ethyldiethanolamine and ethylamine (mixing molar ratio: N-ethyldiethanolamine: ethylamine=1:1) was flowed through the reactor from an upper portion at LHSV=0.5 g/cc-catalyst·h (mixture of N-ethyldiethanolamine and ethylamine) to perform a reaction at 350° C. A reacted gas discharged from the reactor was absorbed into ice-cold water, and then the absorption liquid was analyzed by gas chromatography. Between the initiation of the reaction and 2 hours thereafter, the average yield of 2-(ethylamino) ethanol was 49.9%, and the average conversion rate of N-ethyldiethanolamine was 93.0%.

Example 2

A reaction was performed in the same manner as in Example 1 except that ethylamine was not used. As a result, between the initiation of the reaction and 2 hours thereafter, the average yield of 2-(ethylamino) ethanol was 37.2%, and the average conversion rate of N-ethyldiethanolamine was 79.8%.

Example 3

A reaction was performed in the same manner as in Example 1 except that a 30 wt % aqueous solution of a mixture of N-ethyldiethanolamine and ammonia (mixing molar ratio: N-ethyldiethanolamine:ammonia=1:3) was used in place of the 30 wt % aqueous solution of the mixture of N-ethyldiethanolamine and ethylamine (mixing molar ratio: N-ethyldiethanolamine:ethylamine=1:1). As a result, between the initiation of the reaction and 2 hours thereafter, the average yield of 2-(ethylamino) ethanol was 30.3%, and the average conversion rate of N-ethyldiethanolamine was 89.7%.

Example 4

A reaction was performed in the same manner as in Example 1 except that the reaction was performed using only hydrogen at 30 ml/min as the diluent at a heater temperature of 325° C. As a result, between the initiation of the reaction and 2 hours thereafter, the average yield of 2-(ethylamino) ethanol was 38.6%, and the average conversion rate of N-ethyldiethanolamine was 38.1%.

Example 5

Preparation of Manganese Oxide Catalyst

To 100 g of 15% ammonia water, 186 g of a 46% aqueous solution of manganese nitrate hexahydrate manufactured by Wako Pure Chemical Industries, Ltd. was added to precipitate manganese hydroxide. The generated manganese hydroxide was filtered, and dried at 120° C. for 2 hours, followed by firing in a stream of air at 500° C. for 5 hours to obtain manganese oxide. The obtained manganese oxide was pressed at 70 MPa and then pulverized. The resultant was classified to from 10 to 16 mesh to prepare a manganese oxide catalyst.

Production of 2-(Ethylamino)ethanol

A reaction was performed in the same manner as in Example 1 except that the manganese oxide catalyst was used as the catalyst and the heater temperature was set to 375° C. As a result, between the initiation of the reaction and 2 hours thereafter, the average yield of 2-(ethylamino) ethanol was 47.0%, and the average conversion rate of N-ethyldiethanolamine was 92.5%.

Example 6

A reaction was performed in the same manner as in Example 5 except that ethylamine was not used and the heater temperature was set to 400° C. As a result, between the initiation of the reaction and 2 hours thereafter, the average yield of 2-(ethylamino) ethanol was 45.3%, and the average conversion rate of N-ethyldiethanolamine was 100%.

Example 7

A reaction was performed in the same manner as in Example 3 except that a 30 wt % ethanol solution of a mixture of N-ethyldiethanolamine and ethylamine (mixing molar ratio: N-ethyldiethanolamine:ethylamine=1:1) was used in place of the 30 wt % aqueous solution of the mixture of N-ethyldiethanolamine and ethylamine (mixing molar ratio: N-ethyldiethanolamine:ethylamine=1:1). As a result, between the initiation of the reaction and 2 hours thereafter, the average yield of 2-(ethylamino) ethanol was 38.0%, and the average conversion rate of N-ethyldiethanolamine was 100%.

Example 8

A reaction was performed in the same manner as in Example 5 except that the reaction was performed using nitrogen at 30 ml/min as the diluent at a heater temperature of 350° C. As a result, between the initiation of the reaction and 2 hours thereafter, the average yield of 2-(ethylamino) ethanol was 34.5%, and the average conversion rate of N-ethyldiethanolamine was 94.9%.

Comparative Example 1

A reaction was performed in the same manner as in Example 1 except that a zirconium oxide catalyst RSC-H pellet (cylindrical shape measuring 3.2 mm in diameter by 2.9 mm in length) manufactured by Daiichi Kigenso Kagaku Kogyo Co., Ltd. was used as the catalyst. As a result, between the initiation of the reaction and 2 hours thereafter, the average yield of 2-(ethylamino)ethanol was 2.1%, and the average conversion rate of N-ethyldiethanolamine was 22.2%.

Comparative Example 2

A reaction was performed in the same manner as in Example 1 except that titania powder AMT-100 manufactured by Tayca Corporation was pressed at 70 MPa and pulverized, followed by classification to from 10 to 16 mesh, and the resultant was used as the catalyst. Between the initiation of the reaction and 2 hours thereafter, the average yield of 2-(ethylamino)ethanol was 0.7%, and the average conversion rate of N-ethyldiethanolamine was 100%.

Comparative Example 3

A reaction was performed in the same manner as in Example 1 except that a zinc oxide catalyst FINEX-50 shaped product (extruded product having a diameter of 2.7 mm) manufactured by Sakai Chemical Industry Co., Ltd. was used as the catalyst. As a result, between the initiation of the reaction and 2 hours thereafter, the average yield of 2-(ethylamino) ethanol was 8.0%, and the average conversion rate of N-ethyldiethanolamine was 51.8%.

Comparative Example 4

A reaction was performed in the same manner as in Example 1 except that an active alumina catalyst NKHD-24 (spherical shape having a diameter of from 2 to 4 mm) manufactured by Sumitomo Chemical Co., Ltd. was used as the catalyst. As a result, between the initiation of the reaction and 2 hours thereafter, the average yield of 2-(ethylamino) ethanol was 1.0%, and the average conversion rate of N-ethyldiethanolamine was 100%.

INDUSTRIAL APPLICABILITY

According to the present invention, 2-(ethylamino)ethanol can be obtained by subjecting N-ethyldiethanolamine to the disproportionation reaction in the presence of at least one kind of catalyst selected from the group consisting of the manganese oxide catalyst and the alkali metal hydroxide-supporting zirconium oxide catalyst. 2-(Ethylamino)ethanol is a useful compound to be used in various applications such as a drug, an agricultural chemical, and a functional chemical.

The invention claimed is:

1. A production method for 2-(ethylamino)ethanol, comprising subjecting N-ethyldiethanolamine to a disproportionation reaction in the presence of at least one kind of catalyst selected from the group consisting of a manganese oxide catalyst and an alkali metal hydroxide-supporting zirconium oxide catalyst.

2. A production method for 2-(ethylamino)ethanol according to claim 1, wherein the disproportionation reaction comprises a gas-phase disproportionation reaction.

3. A production method for 2-(ethylamino)ethanol according to claim 1, further comprising allowing a reaction aid to be present in a reaction system.

4. A production method for 2-(ethylamino)ethanol according to claim 3, wherein the reaction aid comprises at least one kind selected from the group consisting of ethylamine and ammonia.

5. A production method for 2-(ethylamino)ethanol according to claim 3, wherein the reaction aid is used in an amount of from 0.5 to 5 mol with respect to 1 mol of N-ethyldiethanolamine.

6. A production method for 2-(ethylamino)ethanol according to claim 1, wherein the disproportionation reaction is performed in presence of at least one kind of gas selected from the group consisting of hydrogen, nitrogen, and oxygen.

7. A production method for 2-(ethylamino)ethanol according to claim 1, wherein the disproportionation reaction is performed at from 300 to 450° C.

8. A production method for 2-(ethylamino)ethanol, comprising absorbing, into water, a reacted gas obtained by subjecting N-ethyldiethanolamine to a disproportionation reaction in presence of at least one kind of catalyst selected from the group consisting of a manganese oxide catalyst and an alkali metal hydroxide-supporting zirconium oxide catalyst.

9. A production method for 2-(ethylamino)ethanol according to claim 8, wherein the disproportionation reaction comprises a gas-phase disproportionation reaction.

10. A production method for 2-(ethylamino)ethanol according to claim 8, further comprising allowing a reaction aid to be present in a reaction system.

11. A production method for 2-(ethylamino)ethanol according to claim 2, wherein the disproportionation reaction is performed in presence of at least one kind of gas selected from the group consisting of hydrogen, nitrogen, and oxygen.

12. A production method for 2-(ethylamino)ethanol according to claim 3, wherein the disproportionation reaction is performed in presence of at least one kind of gas selected from the group consisting of hydrogen, nitrogen, and oxygen.

13. A production method for 2-(ethylamino)ethanol according to claim 4, wherein the disproportionation reaction is performed in presence of at least one kind of gas selected from the group consisting of hydrogen, nitrogen, and oxygen.

14. A production method for 2-(ethylamino)ethanol according to claim 5, wherein the disproportionation reaction is performed in presence of at least one kind of gas selected from the group consisting of hydrogen, nitrogen, and oxygen.

15. A production method for 2-(ethylamino)ethanol according to claim 2, wherein the disproportionation reaction is performed at from 300 to 450° C.

16. A production method for 2-(ethylamino)ethanol according to claim 3, wherein the disproportionation reaction is performed at from 300 to 450° C.

17. A production method for 2-(ethylamino)ethanol according to claim 4, wherein the disproportionation reaction is performed at from 300 to 450° C.

18. A production method for 2-(ethylamino)ethanol according to claim 5, wherein the disproportionation reaction is performed at from 300 to 450° C.

* * * * *